United States Patent
Gershengorn

(10) Patent No.: US 6,365,356 B1
(45) Date of Patent: Apr. 2, 2002

(54) RECEPTORS THAT REGULATE CELL SIGNALING RELATING TO CHEMOKINES

(75) Inventor: Marvin C. Gershengorn, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/271,398

(22) Filed: Mar. 17, 1999

(51) Int. Cl.[7] .................... G01N 33/53; G01N 33/566; C12N 5/00

(52) U.S. Cl. .................. 435/7.1; 435/7.2; 435/7.21; 435/325; 435/326; 435/334; 435/358; 435/361; 435/366; 435/365.1; 435/365

(58) Field of Search ................... 435/7.1, 7.2, 7.21, 435/325, 326, 334, 358, 361, 366, 365.1, 365

(56) References Cited

PUBLICATIONS

Murdoch et al. Chemokine receptors and their role in inflammation and infection dieases, Blood, May 15, 2000. vol. 95, No. 10, pp. 3032–3043.*
Szabo et al. Chemokine Class Differences in Binding to the Duffy antigen–Erythrocyte Chemokine Receptor, Journal of Biological Chemistry, vol. 270, No. 43, pp. 25348–25351, Oct. 1995.*
O'Reilly, et al., Nature Med, 2:689–692 (1996).
Moore, et al., J Invest Med, 46:113–120 (1998).
Jones, et al., J Biol Chem, 272:16166–16169 (1997).
Keane, et al., Proc Assoc Amer Phys, 110:288–296 (1998).
Watson, et al., Science, 268:447–448 (1995).
Tachibana, et al., Nature, 393:591–594 (1998).
Zou, et al., Nature, 393:595–599 (1998).
Nagasawa, et al., Nature, 392:635–638 (1996).
Hadley, et al., Blood, 89:3077–3091 (1997).
Hadley, et al., J. Clin Invest, 94:985–991 (1994).
Heébert, et al., Biochem Cell Biol, 76:1–11 (1998).
Jones, et al., Nature, 396:674–679 (1998).
White, et al., Nature, 396:679–682 (1998).
Kaupmann, et al., Nature 396:683–687 (1998).
Kuner, et al., Science, 283:74–77, Jan. 1, 1999.
Feil, et al., Biochem Biophys Res Commun, 247:38–45 (1998).
Andrew D. Luster, The New England Journal of Medicine, 338:436–446 (1998).

* cited by examiner

Primary Examiner—Gary L. Kunz
Assistant Examiner—Fozia Hamud
(74) Attorney, Agent, or Firm—Hoffmann & Baron, LLP; Irving N. Feit

(57) ABSTRACT

A method for discovering molecules that regulate cell signaling specific to the dual presence of Duffy antigen receptor for chemokines (DARC) and a chemokine receptor selected from the group consisting of a CXC receptor, a CC receptor and a CXXXC receptor, the method comprising providing a cell that co-expresses DARC and the chemokine receptor; incubating the molecules with the cell; measuring the cell signaling in the cell specific to the dual presence of DARC and the chemokine receptor; and determining whether the cell signaling specific to the dual presence of DARC and the chemokine receptor is regulated by the molecules

37 Claims, No Drawings

RECEPTORS THAT REGULATE CELL SIGNALING RELATING TO CHEMOKINES

This invention was made with Government support from the National Institutes of Health (NIH) under Grant Nos. CA-75918 and DK-43036. The Government has certain rights in this invention.

Chemotactic cytokines, also called chemokines, induce cell migration and activation by binding to surface receptors on a large number of target cells. Chemokines are involved in a variety of diseases. For a review, see Luster, New England Journal of Medicine 338, 436 (1998).

The chemokines are peptides that contain four highly conserved Cys residues that form two disulfide bonds, Baggiolini, et al., The New England Journal of Medicine, 338:436–445 (1998). There are several classes of chemokines. The two largest classes are CXC chemokines, in which two highly conserved Cys residues at the peptide amino terminus are separated by any amino acid, and CC chemokines, in which the Cys residues are proximate to one another.

Chemokines act via G protein-coupled receptors (GPCRs). GPCRs represent the largest family of signal-transducing molecules known, and convey signals for a diverse array of extracellular regulatory molecules. By coupling to G proteins and then activating effectors, GPCRs initiate a series of intracellular signal transduction cascades. In a major pathway, chemokine receptors activate phospholipase C to form second messengers, such as inositol 1,4,5-trisphosphate, which mobilizes calcium ion, and 1,2-diacylglycerol, which activates protein kinase C. Other protein kinases are activated by GPCRs and lead to cell proliferation.

A number of GPCRs for chemokines have been cloned. Epstein, The New England Journal of Medicine, 338:436–445. CXC receptors are designated CXCR1, CXCR2, etc. CC receptors are designated CCR1, CCR2, etc.

The CXC chemokines can be subdivided into peptides that contain the sequence Glu-Leu-Arg (ELR) at their amino termini (ELR+) and those that do not (ELR−). In general, CXCRs are activated by ELR+ or ELR− CXC chemokines, but usually not both. In fact, CXC/ELR− chemokines can act as antagonists at receptors for CXC/ELR+ chemokines. For example, interleukin-8 (IL-8) activation of CXCR2 can be antagonized by an analog of PF-4. Jones, et al., Journal of Biological Chemistry 272:16166–16169 (1997).

Chemokine receptors are found on a variety of cells, such as on hematopoietic cells, neurons, astrocytes, epithelial cells, and endothelial cells. The presence of chemokine receptors on these different types of cells suggests various roles for chemokine receptors, such as leukocyte chemotaxis and stimulation of endothelial cell proliferation. Luster, New England Journal of Medicine 338, 436 (1998).

The Duffy antigen receptor for chemokines (DARC) is found on various types of cells, such as endothelial cells and blood cells, including erythrocytes and leukocytes. DARC binds both CXC/ELR+ and CXC/ELR− chemokines. Hadley, et al., J. Amer. Soc. Hematol. 89: 3077–3091 (1997); J. Clin. Invest. 94:985–991 (1994).

DARC does not, however, transduce a signal in activation assays, at least when expressed in transfected cells alone. In fact, DARC is missing some of the highly conserved residues that are known to be important for signaling of the rhodopsin/β-adrenergic subfamily of GPCRs, such as the Asp-Arg-Tyr (DRY) sequence at the intracellular aspect of putative transmembrane helix-3. In a recent review article, Hadley and Peiper stated in a section entitled "The Riddle of DARC Function" that the role of DARC in normal and pathologic physiology remains uncertain. See Blood 89 3077 (1997).

As is apparent from the above, chemokines exhibit a large number of important physiological and pathophysiological functions, such as in angiogenesis. For example, angiogenesis is the proliferation of new blood vessels from preexisting vasculature. Net neovascularization is a balance between the effects of angiogenesis-stimulatory (angiogenic) factors and angiogenesis-inhibitory (angiostatic) factors.

During some pathological conditions, it is desirable to bias the balance between angiogenic factors and angiostatic factors. For example, in order for tumors to grow and metastasize, net angiogenesis must be persistent. Therefore, it is desirable to bias the balance in favor of angiostatic factors in order to inhibit tumor growth.

On the other hand, atherosclerosis is a condition caused by a compromised blood supply. Therefore, it is desirable to bias the balance in favor of angiogenic factors in order to treat atherosclerosis.

There are a number of peptide factors that regulate angiogenesis. For example, vascular endothelial growth factor (VEGF) and basic fibroblast growth factor (bFGF) are angiogenic factors. Angiostatin and endostatin are angiostatic factors.

Chemokines constitute another class of peptides that appear to regulate angiogenesis, Keane, et al., Proc Assoc Amer Phys 110:288–296 (1998). Chemokines have not been studied as intensively as other angiogenic factors, and the receptor(s) that mediates chemokine regulation of angiogenesis and angiostasis has not been identified.

In general, putative angiogenic chemokines are CXC/ELR+, e.g., growth-related protein-α (Gro-α) and IL-8, and putative angiostatic chemokines are CXC/ELR−, e.g., interferon γ-inducible protein-10 (IP-10) and platelet factor-4 (PF-4). Moore, et al., J. Invest. Med. 46:113–120 (1998).

It is likely that stimulation of these pathways by CXC/ELR+ chemokines leads to proliferation of endothelial cells and angiogenesis. The receptor(s) that mediates these angiogenic effects, however, is not known.

Similarly, several CXC/ELR− chemokines are known to be angiostatic factors. The receptor(s) that mediates angiostasis is also not known.

There is considerable uncertainty regarding how chemokine receptors activate angiogenesis. It was suggested by Keane, et al., (Proceeding of the Association of American Physicians, 110:288–296 (1998)), that CXCR2 may mediate the angiogenic effects of IL-8, Watson, et al., Science 268:447–448. However, it is not clear that CXCR2 is expressed on endothelial cells. Moreover, mice that lack CXCR2 appear to have a normal vasculature.

By contrast, CXCR4, the receptor for the CXC/ELR− chemokine stromal cell-derived factor-1 (SDF-1), is found on endothelial cells. Mice lacking CXCR4 have defective vasculogenesis. Tachibana, et al., Nature, 393:591–594 (1998); Zou, et al., Nature, 393:595–599 (1998). Similarly, mice lacking SDF-1 have defective vasculogenesis. Nagasawa, et al., Nature, 382:635–638 (1996).

However, neither of the putative angiogenic chemokines Gro-α and IL-8 (see above) activates CXCR4. Therefore, if CXCR4 is involved in regulating angiogenesis, it cannot be acting alone, or is mediated by an unknown ligand.

Additional uncertainties exist. For example, it is not known whether any known CXC receptor mediates the angiostatic effects of the CXC/ELR− chemokines PF-4 and IP-10. The receptor for IP-10 is CXCR3; however, CXCR3 is not expressed on endothelial cells. Moreover, there is no known GPCR for PF-4.

It is of potential interest in this regard that, as mentioned above, the Duffy antigen receptor for chemokines (DARC) is found on endothelial cells, and binds both CXC/ELR+ and CXC/ELR− chemokines. Hadley, et al., J. Amer. Soc. Hematol. 89: 3077–3091 (1997); J Clin. Invest. 94:985–991 (1994).

The identification of the chemokine receptor that regulates angiogenesis is of potentially enormous value because receptors that regulate angiogenesis and angiostasis are potential targets for drug therapy of many human diseases, including diseases in which angiostasis is desirable, (e.g., cancers) and diseases in which angiogenesis is desirable (e.g., atherosclerosis). The value of such receptors as targets in drug screening, however, cannot be realized, until the receptors have been identified.

It is an object of the present invention to enable the screening for drugs that regulate the activities of chemokine receptors, especially of angiogenesis-mediating chemokine receptors, as well as the receptors that can be used as targets for the drug in such screens.

SUMMARY OF THE INVENTION

These and other objectives as will be apparent to those having skill in the art have been achieved by providing a method for discovering molecules that regulate cell signaling specific to the dual presence of DARC and a chemokine receptor. The method comprises two steps. In the first step, a cell that expresses DARC and a chemokine receptor is provided. The second step involves determining that the molecule regulates cell signaling specific to the dual presence of DARC and the chemokine receptor. The method is particularly suitable for discovering molecules that regulate cell signaling relating to angiogenesis and angiostasis.

The invention also includes cells transfected so that the cell co-expresses DARC and a chemokine receptor; isolated heterodimers comprising DARC and a chemokine receptor; methods for regulating angiogenesis; and methods for determining an angiogenesis signal pathway. The cells transfected to co-express DARC and a chemokine receptor, and the heterodimer comprising DARC and a chemokine receptor, are useful as targets for discovering drugs that regulate angiogenesis.

DETAILED DESCRIPTION OF THE INVENTION

The invention is based on the discovery that the cell signaling for regulating certain activities of chemokine receptors, such as angiogenesis and angiostasis, involves the co-expression of the Duffy antigen receptor for chemokines (DARC) and a chemokine receptor in a cell.

For example, the cell signaling for regulating angiogenesis and angiostasis, involves the co-expression of DARC and a chemokine receptor in an endothelial cell. Such regulation of cell signaling leads to the regulation of angiogenesis in higher organisms, such as manumals.

Chemokine Receptors

A chemokine receptor is any protein that is found on the surface of a cell, and that mediates signaling when it binds to a chemokine. For the purposes of this specification, DARC will not be considered a chemokine receptor.

Chemokines generally bind to specific G protein-coupled receptors on the surface of certain cells, such as hematopoietic cells, neurons, astrocytes, epithelial cells, and endothelial cells. These receptors are classified according to the types of chemokines that bind to them. CXC chemokine receptors include, for example, CXCR1, CXCR2, CXCR3, CXCR4, and CXCR5. CC chemokine receptors include, for example, CCR1, CCR2, CCR2a, CCR2b, CCR3, CCR4, CCR5, CCR6, CCR7, CCR8, CCR9, and CCR10. CXXXC chemokine receptors include $CX_3CR1$.

Method for Discovering Molecules that Regulate Cell Signaling

In one embodiment, the invention includes a method for discovering molecules that regulate cell signaling mediated by chemokine receptors. The method is especially useful for discovering molecules that regulate angiogenesis mediated by chemokine receptors.

The method comprises two steps. The first step is to provide a cell that co-expresses DARC and one or more chemokine receptors, such as the chemokine receptors described above. Any cell that can be made to express DARC and a chemokine receptor, and to transmit a cell signal specific to the dual presence of DARC and the chemokine receptor, can be useful in the method of the invention. For example, the cell can be a procaryotic or eukaryotic cell. Some examples of eukaryotic cells include yeast cells and mammalian cells. Some useful examples of mammalian cells include, for example, COS, CHO, and HEK-293 cells.

Alternatively, the cell may naturally expresses both DARC and a chemokine receptor, particularly CXCR4. When transfected with the appropriate genes, the cell can be made to overexpress DARC and the chemokine receptor. Some examples of cells that naturally expresses both DARC and a chemokine receptor include hematopoietic cells, neurons, astrocytes, epithelial cells, and endothelial cells.

DARC and the chemokine receptors may both be found on the surface of the cells, or both may be found within the cell. Alternatively, one of DARC and the chemokine receptors may be found on the surface of the, cell, while the other is found inside the cell. The two receptors may exist separately from each other, or bound to each other as a heterodimer.

A second step of the method is to determine that the molecule regulates cell signaling specific to the dual presence of DARC and the chemokine receptor. Cell signaling is considered specific to the dual presence of DARC and the chemokine receptor if the molecule regulates cell signaling in the presence of both receptors, but does not regulate substantially the same cell signaling in the absence of one or both of the receptors. For example, the presence of both of the receptors may cause the molecule to eliminate a signal, or to generate a new signal, an increased signal, or a decreased signal.

If the molecule regulates cell signaling specific to the dual presence of DARC and the chemokine receptor, as defined above, in an endothelial cell, the cell signaling is related to angiogenesis or angiostasis. These relationships can be confirmed by administering the molecule to a mammal, and determining the effect on angiogenesis or inflammation in an appropriate in vivo model. The molecules discovered by the method of the invention may either stimulate or inhibit angiogenic cell signaling; or may stimulate or inhibit angiostatic cell signaling.

In order to demonstrate the method, DARC and CXCR4 were transfected into COS-1 cells, so that the cells co-expressed DARC and CXCR4. A second group of COS-1 cells were made to express DARC, but not CXCR4. A third group of COS-1 cells were made to express CXCR4, but not DARC. Signaling due to stromal cell derived factor 1 (SDF-1) and GRO-α was measured in a reporter gene assay using a luciferase gene controlled by a protein kinase C-responsive promoter. GRO-α, which binds to DARC, did not signal via CXCR4 or DARC when either was expressed alone. SDF-1, which is a ligand for CXCR4, signals weakly in the presence of CXCR4 and does not signal via DARC.

In the COS-1 cells that co-express both DARC and CXCR4, GRO-α, which did not signal via CXCR4 or DARC when either receptor was expressed alone, was now found to increase gene transcription. The signal observed when both SDF-1 and GRO-α was present was greater than expected from the signal generated by either SDF-1 or GRO-α alone.

The stimulation or inhibition of cell signaling may occur in the method of the invention by means of any mechanism. For example, the molecules may act as neutral antagonists by competing with an agonist for a receptor. Alternatively, the molecules may act as agonists by activating a receptor.

Another type of antagonist is called a negative antagonist (or inverse agonist). The molecules may act as negative antagonists by directly inhibiting the activity of a basally or constitutively active receptor.

The assay used in the method may be any assay that is capable of determining that the molecule being tested regulates cell signaling specific to the dual presence of DARC and the chemokine receptor. For example, the assay may be a competitive (or displacement) binding assay or an assay that measures signaling, such as the assay described above. Such assays are well known in the art. See, for example, Limbird, LE, Cell Surface Receptors: A Short Course (1986).

For example, in one type of competetive binding assay, DARC, preferably a cell comprising DARC, and a chemokine receptor, preferably a cell comprising a chemokine receptor, is immobilized. A known ligand of DARC, such as, for example, GRO-α; and a known ligand of a chemokine receptor, such as, for example, IL-8 (CXCR2), IP-10 (CXCR3), or SDF-1 (CXCR4), are labelled. Some suitable labels include, for example, radioactive labels, such as $^{32}P$, $^{125}I$, $^{131}I$, and $^{3}H$, and non-radioactive labels, such as enzymes, chromogens, atoms and molecules detectable by electron microscopy, and metal ions detectable by their magnetic properties. The molecule is allowed to compete with the ligand for the immobilized DARC and/or the chemokine receptor. If the molecule binds to one of the receptors, the molecule will compete successfully with, i.e., displace, one of the labelled ligands. The amount of the labelled ligand is measured. Less detection of labelled ligand implies stronger binding of the molecule to one of the ligands.

In a preferred assay, one measures a manifestation of cell signaling following incubation of the molecule being tested with a cell that expresses both DARC and a chemokine receptor. Some suitable manifestations of cell signaling include, for example, an increase in intracellular mediator molecules (cytoplasmic free calcium ion concentration or inositol 1,4,5-trisphosphate levels), activation of specific signaling kinases, or induction of specific reporter genes, such as a luciferase gene. A positive result would be an increase or a decrease in any of these manifestations in cells expressing both DARC and a chemokine receptor when compared to control cells. Control cells are cells expressing neither DARC nor a chemokine receptor, or only one of DARC and a chemokine receptor.

The molecules that are candidates for discovery in accordance with the method of the invention can be any molecule. Two classes of molecules are arbitrarily defined for the purposes of this specification.

Biological molecules include all lipids and polymers of monosaccharides, amino acids and nucleotides having a molecular weight greater than 450. Thus, biological molecules include, for example, oligosaccharides and polysaccharides; oligopeptides, polypeptides, peptides, and proteins; and oligonucleotides and polynucleotides. Oligonucleotides and polynucleotides include, for example, DNA and RNA.

Biological molecules further include derivatives of any of the molecules described above. For example, derivatives of biological molecules include lipid and glycosylation derivatives of oligopeptides, polypeptides, peptides and proteins. Derivatives of biological molecules further include lipid and glycosylated derivatives of oligosaccharides and polysaccharides, e.g. lipopolysaccharides.

Any molecule that is not a biological molecule is considered in this specification to be a small molecule. Accordingly, small molecules include organic compounds, organometallic compounds, salts of organic and organometallic compounds, saccharides amino acids, and nucleotides. Small molecules further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

It is emphasized that small molecules can have any molecular weight. They are merely called small molecules because they typically have molecular weights less than 450. Small molecules include compounds that are found in nature as well as synthetic compounds.

Thus, all molecules are intended to be covered by one or the other of the above arbitrary definitions. For example, the molecule may comprise a biological molecule bonded to a small molecule.

Receptor Combinations Per Se

In another embodiment, the invention includes combinations of DARC and any of the chemokine receptors described above. For example, the combination may comprise a soluble DARC/chemokine receptor heterodimer isolated from cells. Such soluble heterodimers can be prepared by methods known in the art. For example, the heterodimer can be expressed on the surface of appropriate cells, solubilized with detergents, and isolated by affinity chromatography. The cells may be endothelial cells that express the heterodimer naturally, endothelial cells transfected with appropriate genes so that the cells overexpress the heterodimer, or a cell that does not express DARC and a chemokine receptor naturally, but have been transfected with appropriate genes to do so. A preferred soluble heterodimer is DARC/CXCR4.

The combination can also comprise a cell that is transfected with DNA that expresses both DARC and any of the chemokine receptors described above so that the cells co-express both DARC and the chemokine receptor. The cell may be any of the cells described above.

Methods for Regulating Cell Signaling Related to Chemokine Receptors

The discovery that the co-expression of DARC and a chemokine receptor by cells, especially by endothelial cells, is important in the regulation of cell signaling related to chemokine receptors leads to new therapeutic targets for intervention in conditions in which the regulation of such cell signaling is important.

In endothelial cells, the cell signaling is related to the regulation of angiogenesis and angiostasis. Thus, the invention further comprises a method for regulating angiogenesis in a mammal. The method comprises treating the mammal with an effective amount of a molecule that regulates cell signaling specific to the dual presence of DARC and the chemokine receptor co-expressed in any of the cells described above. The molecule may, for example, be discovered in accordance with the method for discovering molecules described above.

The molecule may either inhibit or stimulate angiogenesis. Alternatively, the molecule may stimulate or inhibit angiostasis. Molecules that inhibit angiogenesis or stimulate angiostasis are useful for treating conditions characterized by excessive neovascularization, such as cancers, especially cancers involving solid tumors. Molecules that stimulate angiogenesis or inhibit angiostasis are useful in treating conditions that benefit from neovascularization. Such conditions include, for example, atherosclerosis.

The mammal treated in accordance with the method of the invention may be any mammal, such as farm animals, pet animals, labratory animals, and primates, including humans. Farm animals include, for example, cows, goats, sheep, pigs, and horses. Pet animals include, for example, dogs and cats. Laboratory animals include, for example, rabbits, mice, and rats.

In another embodiment, the invention comprises treating the mammal with a first molecule that regulates DARC and with a second molecule that regulates a chemokine receptor. For example, the first molecule may be an antagonist with respect to DARC, while the second molecule is an antagonist with respect to the chemokine receptor. In another example, the first molecule may be an agonist with respect to DARC, while the second molecule is an agonist with respect to the chemokine receptor.

Some examples of first molecules include, for example, GRO-α and antibodies or antibody fragments that bind specifically to, and regulate, DARC. Some examples of second molecules include, for example, SDF-1 and antibodies or antibody fragments that bind specifically to, and regulate, the chemokine receptor.

Antibodies include fragments of antibodies that bind to the same target as the whole antibody, and have comparable acitivity. For example, fragments may contain one or both Fab fragments or the F(ab')$_2$ fragment. Preferably the antibody fragments contain all six complementarity determining regions of the whole antibody, although fragments containing fewer than all of such regions, such as three, four or five CDRs, may also be functional. Fragments may be prepared by methods described by Lamoyi et al in the Journal of Immunological Methods 56, 235–243 (1983) and by Parham in the Journal of Immunology 131, 2895–2902 (1983).

A preferred antibody fragment is a "single chain Fv" (scFv or single chain antibody), which consists of an antibody heavy chain variable domain linked to an antibody light chain variable domain by a peptide linker that allows the two domains to associate to form a functional antigen binding site (see, for example U.S. Pat. No. 4,946,778, Ladner et al., (Genex); WO 88/09344, Huston et al. (Creative Biomolecules). McCafferty et al describes the display of scFv fragments on the surface of soluble recombinant genetic display packages, such as bacteriophage, in international PCT patent application WO 92/01047, (Cambridge Antibody Teclnology et al.).

Method for Determing a Signal Pathway

In another embodiment, the invention relates to a method for determining a signal pathway. The method comprises providing a cell that expresses DARC and any of the chemokine receptors described above. For determining a signal pathway related to angiogenesis, the preferred chemokine receptor is CXCR4.

A molecule known to regulate cell signaling specific to the dual presence of DARC and the chemokine receptor is then made to contact the cell. The resulting cell signal is related to angiogenesis or angiostasis. The pathway that results from the signaling is determined by methods known in the art. See, for example, Gutkind, J. Biol. Chem. 273, 1839–1842 (1998).

For example, one or more of three major signaling pathways may be involved: 1) receptor tyrosine kinase—Ras—extracellular regulatory kinase-2 (ERK-2); 2) Jun kinase (JNK)/stress-activated protein kinase (SAPK); and 3) p38 mitogen-activated protein kinase (p38MAPK). These, or other, pathways can be monitored by directly measuring the activity(ies) of one or more kinases in the pathway or by measuring the effect of their specific activation on reporter genes that are under control of specific promoter/enhancers activated by a specific transcription factor, such as Jun for the JNK/SAPK pathway or CHOP for the p38MAPK pathway. An increase or decrease in the activity or effect on a reporter gene or an increase or decrease in the transcription of a specific reporter gene by a kinase or a transcription factor, for example, in cells expressing both DARC and a chemokine receptor when they are exposed to molecules that affect both DARC and the chemokine receptor, compared to control cells, indicates that the kinase or transcription factor is involved in the pathway. Control cells could be cells expressing neither DARC nor a chemokine receptor or only one of DARC or a chemokine receptor.

General Methods

Preparing Proteins

Proteins may be prepared by methods known in the art. See, for example, Sambrook, Fritsch and Maniatis (eds) in *Molecular Cloning, A Laboratory Manual,* Second Edition, Cold Spring Harbor Laboratory Press (1989). Such methods include (A) providing DNA that encodes the protein; (B) amplifying or cloning the DNA in a suitable host; (C) expressing the DNA in a suitable host; and (D) optionally, harvesting the protein.

A. Providing DNA

The entire gene or additional fragments of the gene encoding DARC or the chemokine receptor may be isolated using the known DNA sequence or fragments thereof as a probe by methods known in the art. For example, DNA restriction fragments of genomic DNA are identified by Southern hybridization using labelled oligonucleotide probes derived from the known sequence. Alternatively, cDNAs encoding DARC or a chemokine receptor may be prepared from the corresponding RNA or by screening a cDNA library.

If the DNA sequence of DARC or the chemokine receptor is not known, the DNA sequence may be isolated by using the partial amino acid sequence to prepare one or more oligonucleotide probes. The probe is labelled and used to screen a genomic or cDNA library in a suitable vector, such as in phage lambda.

The DNA isolated may be sequenced, and the sequence used to prepare additional oligonucleotide probes. This procedure may be repeated to obtain overlapping fragments until a complete open reading frame is produced.

Sufficient information for preparing the DNA that encodes DARC and chemokine receptors is known in the art, and can be routinely found by persons having ordinary skill. Some of such information is provided below.

For example, the DNA for DARC can be obtained from information in Chaudhuri et al., Proc. Natl. Acad. Sci. USA 90, 10793 (1993).

The DNA for CCR1 can be obtained from information in Neote et al., Cell 72, 415 (1993); Gao et al, J. Exp. Med. 177, 1421 (1993); Charo et al., Proc. Natl. Acad. Sci. USA 91, 2752 (1994) and GeneBank L10918.

The DNA for CCR2, CCR2a, and CCR2b can be obtained from information in Neote et al., Cell 72, 415 (1993); Gao et al., J. Exp. Med. 177, 1421 (1993); Charo et al., Proc. Natl. Acad. Sci. USA 91, 2752 (1994); Kuang et al., J. Biol. Chem. 271, 3975 (1996) and from, GenBank U03882 (CCR2a) and U03905 (CCR2b).

The DNA for CCR3 can be obtained from information in Daugherty et al., J. Exp. Med. 183, 2349 (1996); Ponath et al., J. Exp. Med. 183, 2347 (1996); Combadiere et al., J. Biol. Chem. 270, 16,491 (1995); correction: J. Biol. Chem. 270, 30,235 (1995); and GenBank U51241.

The DNA for CCR4 can be obtained from information in Power et al., J. Biol. Chem. 270, 19,495 (1995) and GenBank X85740.

The DNA for CCR5 can be obtained from information in Legler et al., J. Exp. Med. 187, 655 (1998) and GenBank X91492.

The DNA for CCR6 can be obtained from information in Baba et al., J. Exp. Med. 272, 14,893 (1997).

The DNA for CCR7 can be obtained from information in Yoshida et al., J. Biol. Chem. 272, 13,803 (1997).

The DNA for CCR8 can be obtained from information in Roos et al., J. Biol. Chem. 272 17,251 (1997).

The DNA for CCR9 can be obtained from information in Choe et al., J. Virol. 72, 6113 (1998).

The DNA for CCR10 can be obtained from information in Bonini et al., DNA Cell Biol. 16, 1249 (1997).

The DNA for CXCR1 can be obtained from information in Holmes et al., Science 253, 1278 (1991); Murphy et al., Science 253, 1280 (1991) and GenBank M68932.

The DNA for CXCR2 can be obtained from information in Holmes et al., Science 253, 1278 (1991); Murphy et al., Science 253, 1280 (1991) and GenBank M73969.

The DNA for CXCR3 can be obtained from information in Loetscher et al., J. Exp. Med. 184, 963 (1996) and GenBank X95876.

The DNA for CXCR4 can be obtained from information in Feng et al., Science 272, 872–877 (1996) and GenBank X71635.

The DNA for CXCR5 can be obtained from information in Dobner et al., Eur. J. Immunol. 22, 2795 (1992).

The DNA for $CX_3CR1$ can be obtained from information in Imai et al., Cell 91, 521 (1997) and Combadiere et al., J. Biol. Chem. 273, 23,799 (1998)

B. Amplifying DNA

The DNA obtained may be amplified by methods known in the art. One suitable method is the polymerase chain reaction (PCR) method described by Saiki et al. in Science 239,487 (1988), Mullis et al in U.S. Pat. No. 4,683,195 and by Sambrook, Fritsch and Maniatis (eds) in *Molecular Cloning, A Laboratory Manual,* Second Edition, Cold Spring Harbor Laboratory Press (1989). It is convenient to amplify the clones in the lambda-gt10 or lambda-gt11 vectors using lambda-gt10 or lambda-gt11-specific oligomers as the amplimers (available from Clontech, Palo Alto, Calif.).

C. Cloning and Expressing DNA

The DNA encoding DARC or the chemokine receptor of the invention may be replicated and used to express recombinant protein following insertion into a wide variety of host cells in a wide variety of cloning and expression vectors. The host may be procaryotic or eukaryotic. The DNA may be obtained from natural sources and, optionally, modified. The genes may also be synthesized in whole or in part.

Cloning vectors may comprise segments of chromosomal, non-chromosomal and synthetic DNA sequences. Some suitable prokaryotic cloning vectors include plasmids from *E. coli,* such as cole1, pCR1, pBR322, pMB9, pUC, pKSM, and RP4. Prokaryotic vectors also include derivatives of phage DNA such as M13 fd, and other filamentous single-stranded DNA phages.

Vectors for expressing proteins in bacteria, especially *E.coli,* are also known. Such vectors include the pK233 (or any of the tac family of plasmids), T7, and lambda $P_L$. Examples of vectors that express fusion proteins are PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX); maltose binding protein (pMAL); glutathione S-transferase (pGST)—see Gene 67, 31 (1988) and Peptide Research 3, 167 (1990).

Vectors useful for cloning and expression in yeast are available. A suitable example is the 2u circle plasmid.

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e. shuttle vectors, allow for the isolation and identification of protein coding sequences in procaryotes.

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., $Pho_5$, the promoters of the yeast alpha-mating factors, and promoters derived from polyoma, adenovirts, retrovirus, and simian virus, e.g., the early and late promoters or SV40, and other sequences known to control the expression of genes of prokaryotic or eukaryotic cells and their viruses.

Useful expression hosts include well-known prokaryotic and eukaryotic cells. Some suitable prokaryotic hosts include, for example, *E. coli,* such as *E. coli* SG-936, *E. coli* HB 101, *E. coli* W3110, *E. coli* X1776, *E. coli* X2282, *E. coli* DHI, and *E. coli* MRC1, Pseudomonas, Bacillus, such as *Bacillus subtilis,* and Streptomyces. Suitable eukaryotic cells include yeasts and other fungi, insect cells, animal cells, such as HEK-293, COS cells and CHO cells, human cells and plant cells in tissue culture.

Preparing Antibodies

Polyclonal antibodies are isolated from mammals that have been inoculated with the protein or a functional analog in accordance with methods known in the art. Monoclonal antibodies may be produced by methods known in the art. These methods include the immunological method described by Kohler and Milstein, *Nature* 256:495–497 (1975) and by Campbell (1985); as well as the recombinant DNA method described by Huse et al., *Science* 246:1275–1281 (1989).

EXAMPLES

Example 1

Cell Culture and Transfection. COS-1 cells are maintained in Dulbecco's modified eagle's medium with 5% fetal calf serum and are seeded 1 day prior to transfection at 750,000 cells/100 mm dish. Cells are transfected with pcDNA3.1 (Invitrogen) encoding DARC (5 μg DNA/ml) or with pcDNA3.1 encoding CXCR4 (5 μg DNA/ml), or both using the DEAE-dextran method and maintained in Dulbecco's modified Eagle's medium with with 10% fetal calf serum for 1 day at which time cells are harvested and seeded into 12-well plates at 100,000 cells/well or 24-well plates at 50,000 cells/well in Dulbecco's modified Eagle's medium with 5% fetal calf serum. Other cell lines, such as HEK-293 or CHO cells, can be stably transfected with DARC or CXCR4, or both.

Example 2

Competitive Receptor Binding Studies. One day after reseeding, binding experiments are carried out in balanced salt buffer with cells in monolayer for 1 hour at 37° C. The concentration of [$^{125}$I]Gro-α or [$^{125}$I]SDF-1 is 10 pM and competition is with various concentrations of unlabeled chemokine (usually between $10^{-9}$ and $10^{-6}$ M). The assay can be automated for high throughput assay.

Example 3

Measurement of Cytoplasmic Free Calcium. One day after reseeding, cells are loaded with a fluorescent dye, such as FLUO3, that monitors changes in cytoplasmic free calcium concentration. This assay can be automated for high throughput assay using a fluorimetric imaging plate reader.

Example 4

Inositol Phosphate (IP) Formation. One day after transfection, cells in monolayer in 12- or 24-well plates are labeled with 1 μCi myo-[$^3$H]inositol/ml. Stimulation of IP formation by agonists or inhibition of agonist-stimulated IP formation by antagonist are measured one day later for 1 hour at 37° C. [$^3$H]IPs are measured by ion-exchange chromatography.

Example 5

Reporter Gene Assays. Mammalian expression plasmids, such as the PATH DETECT in vivo signal transduction reporting system (stratagene) containing a gene encoding a reporter enzyme, such as luciferase, under control of specific signal tranduction pathway-associated promoters/enhancers, in cis, i.e., AP-1, or trans, i.e., cJUN, are transiently or stably transfected into cells expressing DARC or CXCR4, or both. Agonists or agonists plus antagonists are added for four hours and the reporter activity measured. This assay can be automated for high throughput assay.

What is claimed is:

1. A method for discovering molecules that regulate cell signaling specific to the dual presence of Duffy antigen receptor for chemokines (DARC) and a chemokine receptor wherein the chemokine receptor is CXCR4, the method comprising:
   providing a cell that co-expresses DARC and the chemokine receptor;
   incubating the molecules with the cell;
   measuring the cell signaling in the cell specific to the dual presence of DARC and the chemokine receptor; and
   determining whether the cell signaling specific to te dual presence of DARC and the chemokine receptor is regulated by the molecules.

2. A method according to claim 1, wherein the cell is an endothelial cell.

3. A method according to claim 1, wherein the cell signaling regulates angiogenesis mediated by chemokine receptors.

4. A method according to claim 1, wherein DARC and the chemokine receptor exist on the surface of the cell.

5. A method according to claim 1 wherein the cell is a procaryotic cell.

6. A method according to claim 1 wherein the cell is a eukaryotic cell.

7. A method according to claim 6 wherein the eukaryotic cell is a yeast cell.

8. A method according to claim 6 wherein the eukaryotic cell is a mammalian cell.

9. A method according to claim 8 wherein the mammalian cell is a human cell.

10. A method according to claim 8, wherein the mammalian cell is a COS, CHO, or HEK-293 cell.

11. A method according to claim 8, wherein the mammalian cell is an endothelial cell.

12. A method according to claim 11, wherein the endothelial cell is transfected to overexpress DARC and the chemokine receptor.

13. A method according to claim 1, wherein the molecule inhibits cell signaling.

14. A method according to claim 1, wherein the molecule stimulates cell signaling.

15. A method according to claim 1, wherein the cell signaling is regulated through a G protein.

16. A method according to claim 1, wherein the molecule is a small molecule.

17. A method according to claim 1, wherein the molecule is a biological molecule.

18. A method according to claim 1, wherein DARC and the chemokine receptor exist a heterodimer.

19. A method for determining a signal transduction pathway in a cell that co-expresses DARC and a chemokine receptor, wherein the chemokine receptor is CXCR4, the method comprising;
   providing a cell that co-expresses DARC and the chemokine receptor;
   providing a molecule known to regulate cell signaling specific to the dual presence of DARC and the chemokine receptor;
   contacting the molecule with the cell;
   measuring the regulation of cell signaling specific to the dual presence of DARC and the chemokine receptor; and
   determining the signal transduction pathway of the regulation in the cell.

20. A method according to claim 19, wherein the cell is an endothelial cell.

21. A method according to claim 20, wherein the cell signaling is related to angiogenesis or angiostasis.

22. A method for discovering molecules that regulate cell signaling specific to the dual presence of DARC and a chemokine receptor, wherein the chemokine receptor is CXCR4, the method comprising:
   providing DARC and labeled ligands of DARC;
   providing the chemokine receptor and labeled ligands of the chemokine receptor;
   contacting the labeled ligands and the receptors with the molecules; and
   determining whether the molecules compete successfully with the ligands, wherein successful competition indicates that the molecules regulate cell signaling specific to the dual presence of DARC and the chemokine receptor.

23. A method according to claim 22, wherein the DARC and/or chemokine receptor exist on a cell.

24. A method according to claim 23, wherein the cell is an endothelial cell.

25. A method according to claim 23, wherein the cell signaling regulates angiogenesis mediated by chemokine receptors.

26. A method according to claim 23 wherein the cell is a procaryotic cell.

27. A method according to claim 23 wherein the cell is a eukaryotic cell.

28. A method according to claim 27 wherein the eukaryotic cell is a yeast cell.

29. A method according to claim 27 wherein the eukaryotic cell is a mammalian cell.

30. A method according to claim 29 wherein the mammalian cell is a human cell.

31. A method according to claim 29 wherein the mammalian cell is a COS, CHO, or HEK-293 cell.

32. A method according to claim 29, wherein the mammalian cell is an endothelial cell which is transfected to overexpress DARC and the chemokine receptor.

33. A method according to claim 22, wherein the molecule inhibits cell signaling.

34. A method according to claim 22, wherein the molecule stimulates cell signaling.

35. A method according to claim 22, wherein the molecule is a small molecule.

36. A method according to claim 22, wherein the molecule is a biological molecule.

37. A method according to claim 23, wherein DARC and the chemokine receptor exist as a heterodimer.

* * * * *